(12) United States Patent
Luerkens et al.

(10) Patent No.: US 10,811,329 B2
(45) Date of Patent: Oct. 20, 2020

(54) CERAMIC SUBSTRATE AND METHOD FOR PRODUCING A CERAMIC SUBSTRATE

(71) Applicant: KONINKLIJKE PHILIPS N.V., Eindhoven (NL)

(72) Inventors: Peter Luerkens, Aachen (DE); Albert Garcia Tormo, Eindhoven (NL); Ulf Mueter, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/548,792

(22) PCT Filed: Feb. 10, 2016

(86) PCT No.: PCT/EP2016/052855
§ 371 (c)(1),
(2) Date: Aug. 4, 2017

(87) PCT Pub. No.: WO2016/131693
PCT Pub. Date: Aug. 25, 2016

(65) Prior Publication Data
US 2018/0040528 A1    Feb. 8, 2018

(30) Foreign Application Priority Data
Feb. 17, 2015    (EP) .................................... 15155315

(51) Int. Cl.
*H01L 23/12* (2006.01)
*H01L 23/15* (2006.01)
(Continued)

(52) U.S. Cl.
CPC .............. *H01L 23/15* (2013.01); *C04B 35/10* (2013.01); *C04B 35/457* (2013.01);
(Continued)

(58) Field of Classification Search
None
See application file for complete search history.

(56) References Cited

U.S. PATENT DOCUMENTS 7,279,771 B2 * 10/2007 Sunohara .......... H01L 23/49822
174/255
7,521,878 B2 * 4/2009 Green .................. H05B 39/045
315/291
(Continued)

FOREIGN PATENT DOCUMENTS

DE         3033881 A1    4/1982
DE     102008061636 A1    6/2009
(Continued)

OTHER PUBLICATIONS

"DC-Link Capacitors", Nov. 1, 2011.

*Primary Examiner* — Hung K Vu
(74) *Attorney, Agent, or Firm* — Larry Liberchuk (57) ABSTRACT

The present invention relates to a ceramic substrate (100) comprising: a front side (100-1), which comprises: i) a power semiconductor (102-1, . . . , 102-$n$); and ii) a first metallic layer (104) comprising at least one first metallic plane contact (104-1, . . . , 104-$n$), which is configured to connect the power semiconductor (102-1, . . . , 102-$n$) to a first terminal (105-1, . . . , 105-$n$) on an edge (100-3) of the ceramic substrate (100); a back side (100-2), which comprises: i) a capacitor (103) which is attached to a ii) second metallic layer (108) comprising at least one second metallic plane contact (108-1, . . . , 108-$n$), which is configured to connect the capacitor (103) to a second terminal (107-1, . . . , 107-$n$) on the edge (100-3) of the ceramic substrate (100); and a metallic frame (110), which is configured to connect the first metallic layer (104) to the second metallic layer (108).

13 Claims, 4 Drawing Sheets

(51) Int. Cl.
*H01L 23/498* (2006.01)
*H01L 23/50* (2006.01)
*H01L 25/07* (2006.01)
*C04B 35/10* (2006.01)
*C04B 35/457* (2006.01)
*H01L 27/08* (2006.01)

(52) U.S. Cl.
CPC ........ *H01L 23/49811* (2013.01); *H01L 23/50* (2013.01); *H01L 25/072* (2013.01); *H01L 27/0805* (2013.01); *H01L 2224/48227* (2013.01); *H01L 2224/49111* (2013.01); *H01L 2224/49175* (2013.01); *H01L 2924/13055* (2013.01); *H01L 2924/13091* (2013.01); *H01L 2924/19041* (2013.01); *H01L 2924/19106* (2013.01)

(56) References Cited

U.S. PATENT DOCUMENTS

| | | | |
|---|---|---|---|
| 8,885,374 | B2* | 11/2014 | Zhang ................. H02M 7/483 363/131 |
| 2009/0152714 | A1 | 6/2009 | Yamagishi et al. |
| 2010/0328833 | A1 | 12/2010 | Frisch |
| 2012/0223444 | A1* | 9/2012 | Yamagishi ............ H01L 23/315 257/787 |
| 2013/0229777 | A1 | 9/2013 | Otremba |
| 2014/0152373 | A1 | 6/2014 | Romas, Jr. |

FOREIGN PATENT DOCUMENTS

| | | |
|---|---|---|
| EP | 0971412 A2 | 1/2000 |
| JP | 2009170941 A | 7/2009 |
| JP | 05241344 B2 | 7/2013 |
| WO | 2013018811 A1 | 2/2013 |
| WO | 2013089242 A1 | 6/2013 |
| WO | 2014091608 A1 | 6/2014 |

* cited by examiner

CERAMIC SUBSTRATE AND METHOD FOR PRODUCING A CERAMIC SUBSTRATE

CROSS-REFERENCE TO PRIOR APPLICATIONS

This application is the U.S. National Phase application under 35 U.S.C. § 371 of International Application No. PCT/EP2016/052855, filed on Feb. 10, 2016, which claims the benefit of European Patent Application No. 15155315.3, filed on Feb. 17, 2015. These applications are hereby incorporated by reference herein.

FIELD OF THE INVENTION

The present invention relates to the field of semiconductor device packaging. In particular, the present invention relates to a ceramic substrate and a method for producing a ceramic substrate.

BACKGROUND OF THE INVENTION

High-power high-frequency converters with half- or full-bridge topology have parasitic inductance loops including the direct current, DC-bus capacitor and the half-bridge leg. When a half-bridge switching over the load current from one of the two switches is performed to the other one, the load current has to be redirected to a different current track, thus leaving the track including the first switch and engaging the second switch.

In such a situation it is important to keep both current paths as close as possible, in order to avoid parasitic inductance which leads to overvoltage and additional losses in the switches due to the inductive effect and due to the transition of the current from one path to the other path.

SUMMARY OF THE INVENTION

There may be a need to improve ceramic substrates for semiconductor power modules.

These needs are met by the subject-matter of the independent claims. Further exemplary embodiments are evident from the dependent claims and the following description.

An aspect of the present invention relates to a ceramic substrate comprising: a) a front side, which comprises: i) a power semiconductor; and ii) a first metallic layer comprising at least one first metallic plane contact, which is configured to connect the power semiconductor to a first terminal on an edge of the ceramic substrate; b) a back side, which comprises: i) a capacitor which is attached to a ii) second metallic layer comprising at least one second metallic plane contact, which is configured to connect the capacitor to a second terminal on the edge of the ceramic substrate; and a metallic frame, which is configured to connect the first metallic layer to the second metallic layer and wherein the second metallic layer is configured to form a back side current path on the back side of the ceramic substrate, the back side current path corresponding to a switched current path on the front side as provided by the first metallic layer.

In other words, the present invention provides a configuration for a half-bridge module which carries the DC-link-capacitor in its back side. In other words, the first metallic layer provides a path for a current of a half-bridge power module.

A further, second aspect of the present invention relates to a power semiconductor module comprising a ceramic substrate according to the first aspect of the invention or according to any implementation form of the first aspect of the present invention.

A further, third aspect of the present invention relates to a method for producing a ceramic substrate according to the first aspect of the present invention or according to any implementation form of the first aspect of the present invention.

The method comprises the following steps of:
a) providing a front side, which comprises a power semiconductor and a first metallic layer, comprising at least one first metallic plane contact, which is configured to connect the power semiconductor to a first terminal on an edge of the ceramic substrate;
b) providing a back side, which comprises a first capacitor and a second metallic layer comprising at least one second metallic plane contact, which is configured to connect the capacitor to a second terminal on the edge of the ceramic substrate; and
c) providing a metallic frame, which is configured to connect the first metallic layer to the second metallic layer and wherein the second metallic layer forms a back side current path on the back side, the back side current path corresponding to a switched current path on the front side as provided by the first metallic layer.

This advantageously allows minimizing the effect of parasitic inductance of the semiconductor power module during switching of the power semiconductors.

According to an exemplary embodiment of the present invention, the second metallic layer is configured to form the back side current path on the back side, the back side current path providing a back side current neutralizing a switching current on the front side. This advantageously allows further minimizing the parasitic inductance.

According to an exemplary embodiment of the present invention, the back side of the ceramic substrate further comprises a second capacitor. This advantageously allows further increasing the energy storage capability of the capacitor arrangement.

According to an exemplary embodiment of the present invention, the first capacitor and the second capacitor are connected in series.

This advantageously allows forming a sufficient voltage capability for the intended design.

According to an exemplary embodiment of the present invention, the first capacitor and the second capacitor are direct current, DC-link capacitors. By connecting the mid-potential of the capacitors with the midpoint of the half-bridge the capacitors work as snubber capacitors. In this case external DC-link capacitors are to be used.

According to an exemplary embodiment of the present invention, the second terminal is a terminal used for external snubber capacitors.

According to an exemplary embodiment of the present invention, the metallic frame is configured to form an electrical connection to an external circuit.

According to an exemplary embodiment of the present invention, the metallic frame is a dual side metallic frame.

According to an exemplary embodiment of the present invention, the metallic frame is a lead-frame.

These and other aspects of the present invention will become apparent from and be elucidated with reference to the embodiments described hereinafter.

BRIEF DESCRIPTION OF THE DRAWINGS

A more complete appreciation of the present invention and the attendant advantages thereof will be more clearly understood by reference to the following schematic drawings, which are not to scale, wherein.

DETAILED DESCRIPTION OF EMBODIMENTS

The illustration in the drawings is purely schematically and does not intend to provide scaling relations or size information. In different drawings or figures, similar or identical elements are provided with the same reference numerals. Generally, identical parts, units, entities or steps are provided with the same reference symbols in the description.

The ceramic substrate 100 may be used in the area of power semiconductor modules, of half- or full-bridge configurations but also single ended converter types, where one of the two switches is replaced by a diode (buck-converter module, boost-converter module, etc.).

The ceramic substrate 100 may be used in converter modules, which are completely submerged in cooling liquids, because the entire backside area can be easily used for placement of capacitors and function metallization. Some configurations (e.g. in air) may require using a heat-sink; a certain area in the module may be then reserved to attach the heat-sink as well.

The present invention uses a metallization, that connects the power semiconductors to terminals at the edge of the substrate, and capacitors and a metallization on the backside of the substrate, forming a current path for an AC current on the back side which reiterates the shape of the switched current path on the front side, and a dual side lead-frame that connects the metallization of the front side and the back-side at the edge of the substrate, and forming simultaneously an electrical connection to the surrounding circuit.

By this arrangement, a dual-layer structure is created, in which the change of the current path is again just a transition from one layer to another layer, so the main determining factor for the gap between the two current paths is no longer the lateral extension of the semiconductor placement, but the thickness of the substrate.

The area, which is a measure for the remaining inductance, is largely avoided by offering a second path for the superimposed current on the back side of the module.

The remaining inductance is only determined by the thickness of the substrate. Further extensions of this concept include addition of terminals for snubber capacitors in half-bridge configuration which, in case of split DC capacitor can be favorably connected at the mid-point.

The present invention provides a remaining inductance that is only determined by the thickness of the ceramic substrate, as later shown in FIG. 3.

The present invention provides a dual-sided lead frame, a metallization on the back side reiterating the switching current pattern on front side, DC bus capacitors directly in the reiterated loop. The DC capacitors being part of the low inductance path are arranged in maximum proximity of the switching element (on their back side), and the current routing is designed such that the induction loop areas of all switching currents are minimal (only the thickness of the substrate), instead of using a remote DC capacitor with a special interconnect.

Instead of vias, the present invention may propose using the anyway required lead-frame of the module to create interconnects between front and back side a place the DC capacitors on the back side. Thereby, the present invention can avoid drilling holes into brittle and hard ceramic materials, which would be expensive and introducing reliability risks again.

The present invention advantageously proposes that the ceramic substrate 100 may itself form the heatsink of the system, as such the ceramic substrate 100 may be free-standing in a coolant (e.g. dielectric oil).

Figure 1:
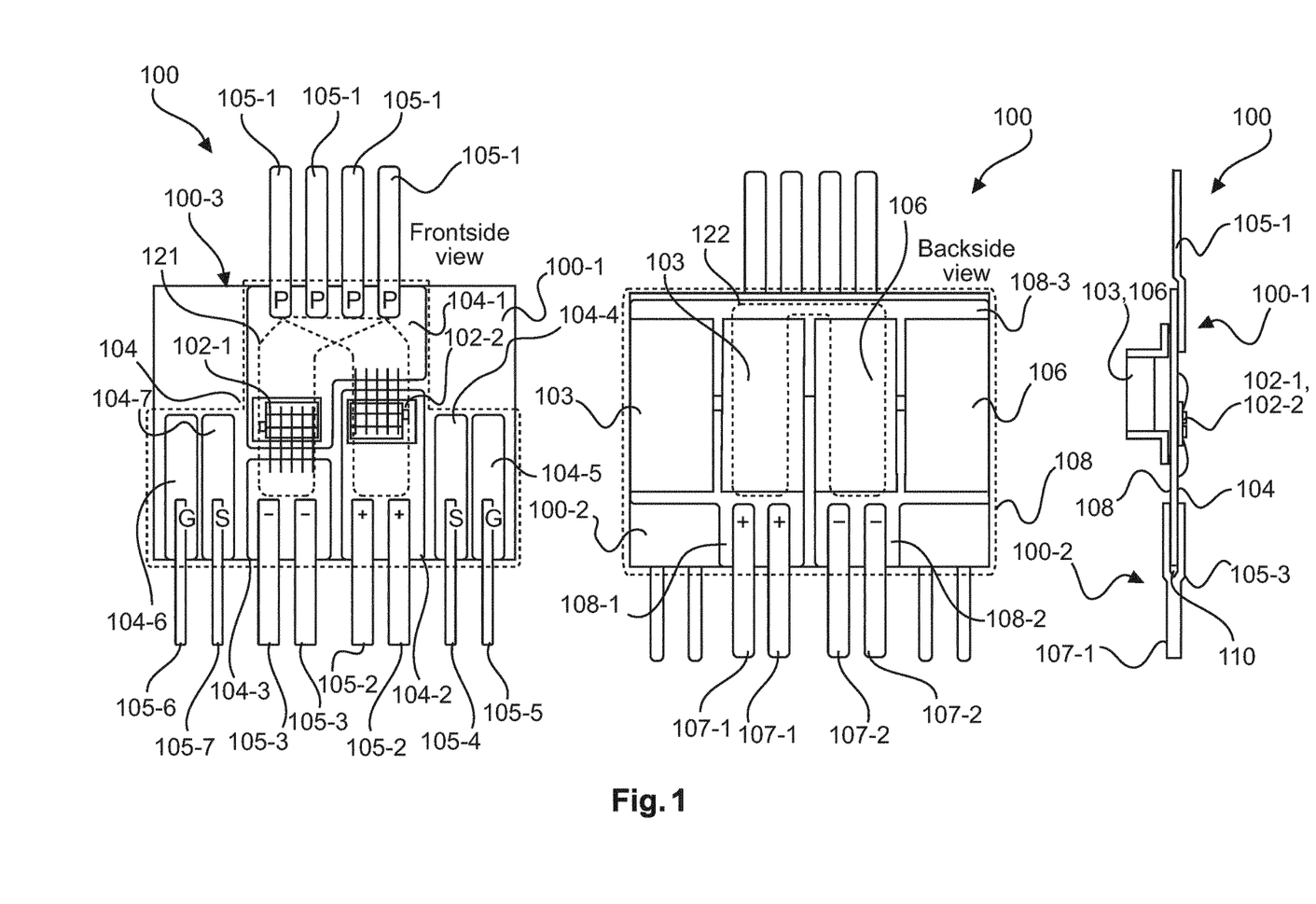
FIG. 1 shows a schematic diagram of a ceramic substrate according to an exemplary embodiment of the present invention.

FIG. 1 shows a ceramic substrate 100 according to an exemplary embodiment of the present invention.

FIG. 1 shows a front side view of the ceramic substrate 100 on the left, a backside view in the middle, and a cross section view of the ceramic substrate 100 on the right.

The ceramic substrate 100 may comprise a front side 100-1, a back side 100-2, an edge 100-3, and a metallic frame 110.

According to an exemplary embodiment of the present invention, the ceramic substrate 100 may comprise technical ceramics, for instance, oxides of alumina, beryllia, ceria, zirconia, nonoxides, or the ceramic substrate 100 may comprise technical ceramics like carbide, boride, nitride, silicide or composite materials as for instance particulate reinforced ceramics, fiber reinforced ceramics, combinations of oxides and nonoxides.

According to an exemplary embodiment of the present invention, the ceramic substrate 100 may comprise aluminium oxide, a chemical compound of aluminium and oxygen with the chemical formula $Al_2O_3$, or aluminum nitride, or beryllium oxide (BeO), also known as beryllia, or silicon carbide (SiC), also known as carborundum.

According to an exemplary embodiment of the present invention, the edge 100-3 of the ceramic substrate 100 may be defined as a joining boundary line between the front side 100-1 and the back side 100-2 of the ceramic substrate 100. In other words, the edge 100-3 of the ceramic substrate 100 may be defined as the place where the front side 100-1 and the back side 100-2 of the ceramic substrate 100 meet.

The front side 100-1 of the ceramic substrate 100 may comprise a power semiconductor 102-1, . . . , 102-n and a first metallic layer 104.

According to an exemplary embodiment of the present invention, the front side 100-1 of the ceramic substrate 100 may comprise at least two power semiconductors 102-1 and 102-2.

According to an exemplary embodiment of the present invention, the power semiconductor 102-1, . . . , 102-n may be a switch or diode in power electronics, a power diode, power thyristor, or power metal oxide semiconductor field-effect transistor, MOSFET, or an insulated-gate bipolar transistor, IGBT.

The first metallic layer 104 may comprise at least one first metallic plane contact 104-1, . . . , 104-n, which is configured to connect the power semiconductor 102-1, . . . , 102-n to a first terminal 105-1, . . . , 105-n on an edge 100-3 of the ceramic substrate 100. For instance, the power semiconductor 102-1, . . . , 102-n may be connected by three different metallic plane contacts 104-1, 104-2, 104-3 to three different terminals 105-1, 105-2, 105-3.

According to an exemplary embodiment of the present invention, the first metallic layer 104 may comprise three first metallic plane contacts 104-1, 104-2, 104-3.

The back side 100-2 may comprise a first capacitor 103 and a second metallic layer 108.

According to an exemplary embodiment of the present invention, the back side 100-2 may comprise a first capacitor 103 and a second capacitor 106.

The second metallic layer 108 may comprise at least one second metallic plane contact 108-1, ..., 108-n, which is configured to connect the capacitor 103 to a second terminal 107-1, ..., 107-n on the edge 100-3 of the ceramic substrate 100.

According to an exemplary embodiment of the present invention, the second metallic layer 108 may comprise two second metallic plane contacts 108-1, 108-2.

According to an exemplary embodiment of the present invention, the first metallic layer 104 and/or the second metallic layer 108 may comprise copper or aluminum or a metallic alloy comprising copper or aluminum.

The metallic frame 110 may be configured to connect the first metallic layer 104 and the second metallic layer 108.

According to an exemplary embodiment of the present invention, the metallic frame 110 may comprise lead or copper or aluminum.

According to an exemplary embodiment of the present invention, the second metallic plane contact 108-1, ..., 108-n may be configured to form a back side current path 122 on the back side 100-2 of the ceramic substrate 100. The back side current path 122 may correspond in its shape to a switched current path 121 on the front side 100-1 as provided by the first metallic plane contact 104-1, ..., 104-n.

In other words, the back side current path 122 may overlap with the switched current path 121 in terms of a ratio, for instance, between 0.6 to 1, when the overlap of the area of the back side current path 122 and the switched current path 121 is considered from a direction orthogonal to the main plane of the ceramic substrate 100, i.e. the view direction as used for the front side view or as used for the back side view.

According to an exemplary embodiment of the present invention, the second metallic plane contact 108-1, ..., 108-n may be configured to form the back side current path 122 on the back side 100-2, the back side current path 122 providing a back side current neutralizing a switching current on the front side 100-1.

According to an exemplary embodiment of the present invention, the ceramic substrate 100 is configured to carry on the front side 100-1 power semiconductors 102-1, ..., 102-n and a metallization in form of the first metallic plane contact 104-1, ..., 104-n, that connects the power semiconductors 102-1, ..., 102-n to terminals at the edge 100-3 of the substrate 100.

The ceramic substrate 100 may further carry capacitors 103, 106 and a metallization in form of the second metallic plane contact 108-1, ..., 108-n on the backside 100-2 of the ceramic substrate, forming a current path in form of the back side current path 122 for an AC current on the back side which reiterates the shape of the switched current path in form of the current path 121 on the front side 100-1.

The ceramic substrate 100 may further comprise a dual side lead-frame in form of the metallic frame 110 that connects the metallization of the front side and the back-side at the edge of the substrate, and forming simultaneously an electrical connection to the surrounding circuit.

By this arrangement, a dual-layer structure is created, in which the change of the current path is again just a transition from one layer to another layer, so the main determining factor for the gap between the two current paths is no longer the lateral extension of the semiconductor placement, but the thickness of the substrate.

According to an exemplary embodiment of the present invention, a second path is offered for the superimposed current on the back side 100-2 of the module in form of the ceramic substrate 100. This arrangement is shown in FIG. 1. On the backside 100-2 another metallization is formed two which the DC bus capacitors area attached.

Figure 2:
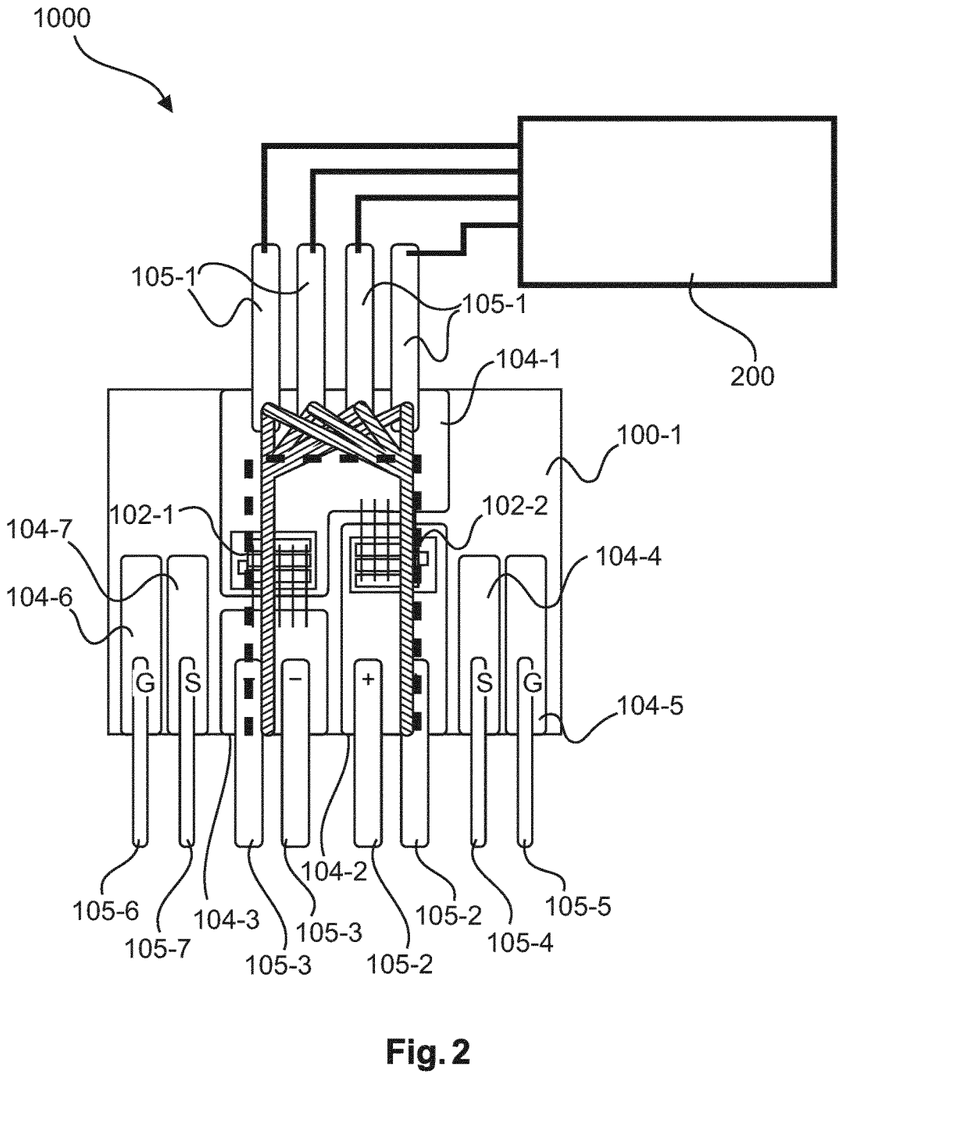
FIG. 2 shows a schematic diagram of a power semiconductor module according to an exemplary embodiment of the present invention.

According to an exemplary embodiment of the present invention, two DC bus capacitors are connected in series, to form a sufficient voltage capability for the intended design. Any capacitor configuration is available as long as the AC current path on the back side 100-2 reflects the switching current path on the front side 100-1. A dual sided lead-frame in form of the metallic frame 110 for the connection to the DC bus at the lower edge forms the connection between the two sides. In FIG. 2, the superimposed current is shown as a line with a dashed pattern, indicating that the current is flowing on the back side.

FIG. 2 shows a schematic diagram of a power semiconductor module according to an exemplary embodiment of the present invention.

FIG. 2 shows a front side view of the ceramic substrate 100. According to an exemplary embodiment of the present invention, a power semiconductor module 1000 may comprise a ceramic substrate 100, wherein the metallic frame 110 is configured to form an electrical connection to an external circuit 200. Not all electrical connections from the ceramic substrate 100 to the external circuit 200 are shown.

The further reference signs in FIG. 2 were already described in the description of FIG. 1.

Figure 3:
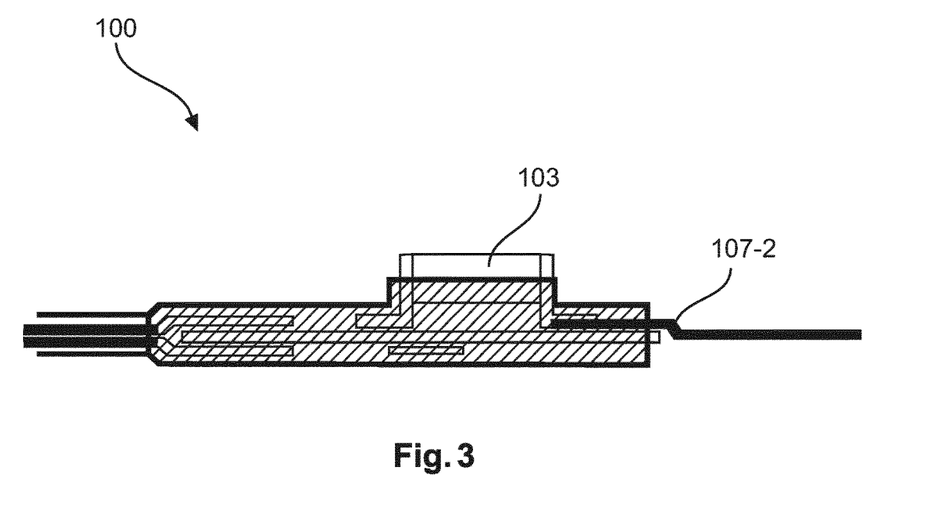
FIG. 3 shows a schematic diagram of a ceramic substrate according to an exemplary embodiment of the present invention.

FIG. 3 shows a schematic diagram of a ceramic substrate according to an exemplary embodiment of the present invention.

FIG. 3 shows a cross section with remaining inductive loop area, indeed, the area has not gone entirely, as shown enlarged in FIG. 3. The cross-section reveals that the thickness of the substrate is now responsible for the remaining inductance. By this, the lateral extension is not of relevance anymore, so that as many as desired devices comprising the ceramic substrate 100 can be connected in parallel.

The further reference signs as present in FIG. 3 were already described in the description with respect to FIG. 1.

Figure 4:
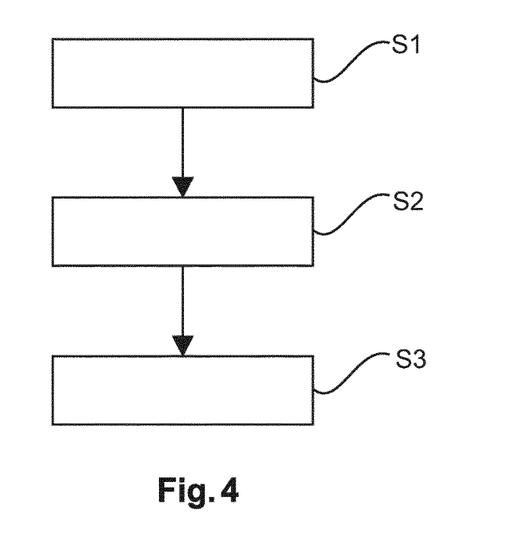
FIG. 4 shows a schematic flow-chart diagram of a method for producing a ceramic substrate according to an exemplary embodiment of the present invention.

FIG. 4 shows a schematic flow-chart diagram of a method for producing a ceramic substrate according to an exemplary embodiment of the present invention.

The method for producing a ceramic substrate 100 may comprise the following steps of:

a) providing S1 a front side 100-1, which comprises a power semiconductor 102-1, ..., 102-n and a first metallic layer 104, comprising at least one first metallic plane contact 104-1, ..., 104-n, which is configured to connect the power semiconductor 102-1, ..., 102-n to a first terminal 105-1, ..., 105-n on an edge 100-3 of the ceramic substrate 100;

b) providing S2 a back side 100-2, which comprises a first capacitor 103 and a second metallic layer 108 comprising at least one second metallic plane contact 108-1, ..., 108-n, which is configured to connect the capacitor 103 to a second terminal 107-1, ..., 107-n on the edge 100-3 of the ceramic substrate 100; and c) providing S3 a metallic frame 110, which is configured to connect the at least one first metallic layer 104 to the at least one second metallic layer 108.

Figure 5:
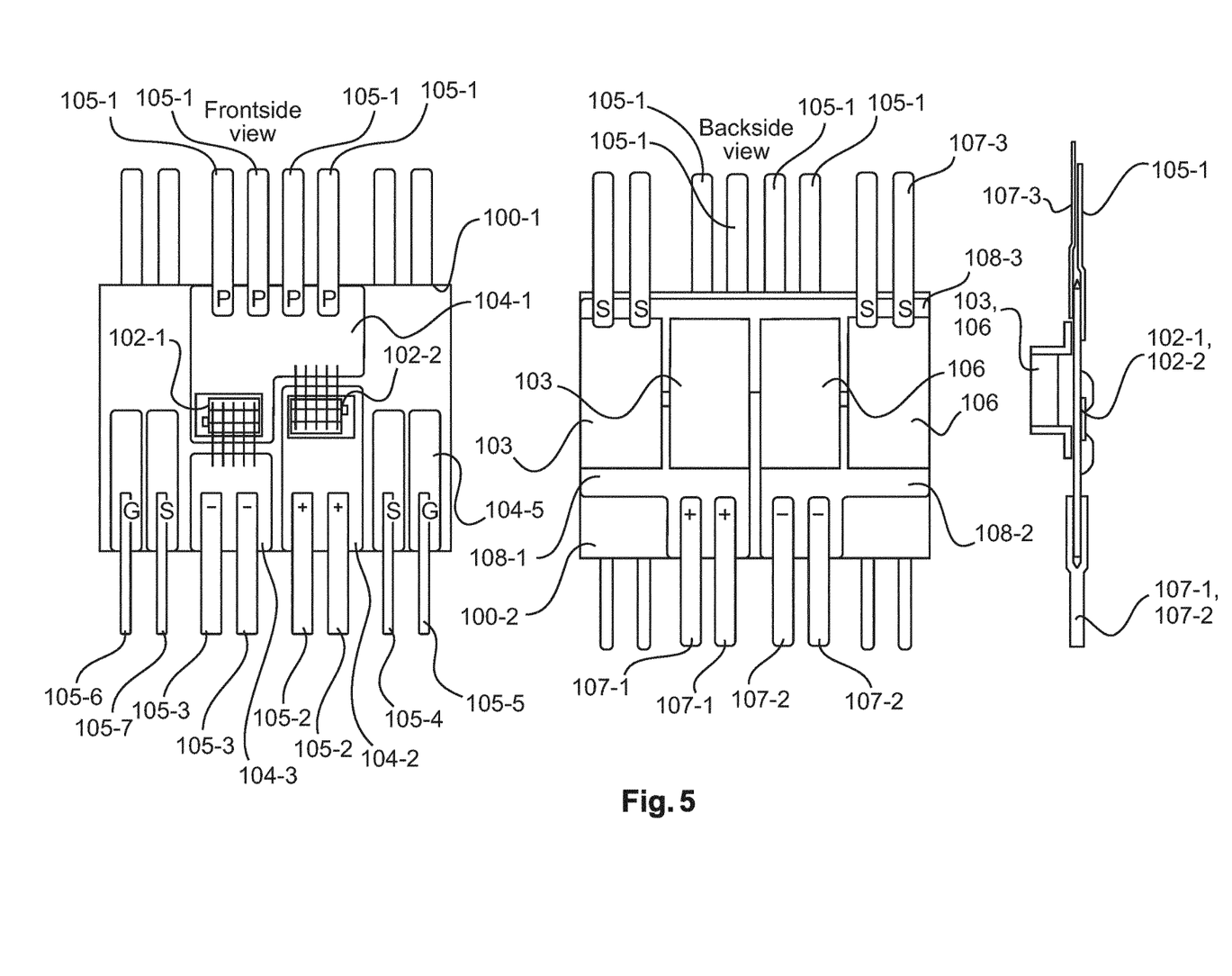
FIG. 5 shows a schematic diagram of a ceramic substrate according to an exemplary embodiment of the present invention.

FIG. 5 shows a schematic diagram of a ceramic substrate according to an exemplary embodiment of the present invention.

FIG. 5 shows a front side view of the front side 100-1 of the ceramic substrate 100 on the left, a backside view of the back side 100-2 in the middle, and a cross section view of the ceramic substrate 100 on the right.

According to an exemplary embodiment of the present invention, snubber capacitor terminals tapped to mid-point of DC bus capacitor may be used.

According to an exemplary embodiment of the present invention, an addition of second terminals 107-3 for snubber capacitors in half-bridge configuration can be used which, in case of split DC capacitors, can be favorably connected at the mid-point.

The further reference signs as present in FIG. 5 were already described in the description with respect to FIG. 1.

It has to be noted that embodiments of the present invention are described with reference to different subject-matters. In particular, some embodiments are described with reference to method type claims whereas other embodiments are described with reference to the device type claims.

However, a person skilled in the art will gather from the above and the foregoing description that, unless otherwise notified, in addition to any combination of features belonging to one type of the subject-matter also any combination between features relating to different subject-matters is considered to be disclosed within this application.

However, all features can be combined providing synergetic effects that are more than the simple summation of the features.

While the present invention has been illustrated and described in detail in the foregoing description and the drawings, such illustration and description are to be considered illustrative or exemplary and not restrictive; the present invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A ceramic substrate comprising:
   a front side, comprising:
      a power semiconductor; and
      a first metallic layer comprising at least one first metallic plane contact configured to connect the power semiconductor to a first terminal on an edge of the ceramic substrate;
   a back side, comprising:
      a capacitor; and
      a second metallic layer attached to the capacitor, the second metallic layer comprising at least one second metallic plane contact configured to connect the capacitor to a second terminal on the edge of the ceramic substrate;
   a metallic frame configured to connect the at least one first metallic layer to the at least one second metallic layer; and
   wherein the second metallic layer is configured to form a back side current path on the back side of the ceramic substrate, the back side current path corresponding to a switched current path on the front side as provided by the first metallic layer.

2. The ceramic substrate according to claim 1, wherein the second metallic layer is configured to form the back side current path on the back side, the back side current path providing a back side current neutralizing a switching current on the front side.

3. The ceramic substrate according to claim 1, wherein the back side of the ceramic substrate further comprises a second capacitor.

4. The ceramic substrate according to claim 3, wherein the first capacitor and the second capacitor are connected in series.

5. The ceramic substrate according to claim 4, wherein the first capacitor and the second capacitor are snubber capacitors if the mid-potential of the capacitors is connected to the midpoint of the half-bridge.

6. The ceramic substrate according to claim 3, wherein the first capacitor and the second capacitor are direct current, DC-link capacitors.

7. The ceramic substrate according to claim 6, wherein the second terminal is a terminal used for external snubber capacitors.

8. The ceramic substrate according to claim 3, wherein the metallic frame is configured to form an electrical connection to an external circuit.

9. The ceramic substrate according to claim 3, wherein the metallic frame is a dual side metallic frame.

10. The ceramic substrate according to claim 1, wherein the metallic frame is a lead-frame.

11. A power semiconductor module comprising a ceramic substrate comprising:
   a front side, comprising:
      a power semiconductor; and
      a first metallic layer comprising at least one first metallic plane contact configured to connect the power semiconductor to a first terminal on an edge of the ceramic substrate;
   a back side, comprising:
      a capacitor; and
      a second metallic layer attached to the capacitor, the second metallic layer comprising at least one second metallic plane contact configured to connect the capacitor to a second terminal on the edge of the ceramic substrate;
   a metallic frame configured to connect the at least one first metallic layer to the at least one second metallic layer; and
   wherein the second metallic layer is configured to form a back side current path on the back side of the ceramic substrate, the back side current path corresponding to a switched current path on the front side as provided by the first metallic layer.

12. A method for producing a ceramic substrate, the method comprising:
   providing a front side, which comprises a power semiconductor and a first metallic layer, comprising at least one first metallic plane contact, which is configured to connect the power semiconductor to a first terminal on an edge of the ceramic substrate;
   providing a back side, which comprises a first capacitor and a second metallic layer comprising at least one second metallic plane contact, which is configured to connect the capacitor to a second terminal on the edge of the ceramic substrate; and providing a metallic frame, which is configured to connect the first metallic layer to the second metallic layer; and wherein the second metallic layer forms a back side current path on the back side, the back side current path corresponding to a switched current path on the front side as provided by the first metallic layer.

13. The method according to claim 12, wherein the second metallic layer forms the back side current path on the back side, the back side current path providing a back side current neutralizing a switching current on the front side.

* * * * *